(12) United States Patent
Kim et al.

(10) Patent No.: US 7,847,124 B2
(45) Date of Patent: Dec. 7, 2010

(54) ALANINE RACEMASE CHIRAL BINAPHTHOL DERIVATIVE WITH POWERFUL HYDROGEN BOND DONOR, AND OPTICAL RESOLUTION AND OPTICAL TRANSFORMATION METHODS USING THE SAME

(75) Inventors: Kwan Mook Kim, Seoul (KR); Lijun Tang, Seoul (KR)

(73) Assignee: Green Formula Co., Ltd., Seoul (KR)

( * ) Notice: Subject to any disclaimer, the term of this patent is extended or adjusted under 35 U.S.C. 154(b) by 208 days.

(21) Appl. No.: 12/028,566

(22) Filed: Feb. 8, 2008

(65) Prior Publication Data

US 2009/0023931 A1    Jan. 22, 2009

(30) Foreign Application Priority Data

Jul. 20, 2007    (KR) .................. 10-2007-0072598

(51) Int. Cl.
*C07C 277/00*    (2006.01)

(52) U.S. Cl. .................. 564/237; 564/236; 564/230

(58) Field of Classification Search .................. 564/237, 564/236, 230
See application file for complete search history.

(56) References Cited

U.S. PATENT DOCUMENTS 7,268,252 B2 *    9/2007    Kim et al. .................. 562/553

FOREIGN PATENT DOCUMENTS

| JP | 02-040344 | 2/1990 |
| JP | 2000336097 | 12/2000 |
| KR | 20040080034 | 9/2004 |
| KR | 20060088489 | 8/2006 |
| WO | WO-2004096753 A1 | 11/2004 |

* cited by examiner

*Primary Examiner*—Rei-tsang Shiao
(74) *Attorney, Agent, or Firm*—Rabin & Berdo, P.C.

(57) ABSTRACT

Disclosed is an alanine racemase chiral binaphthol derivative having the ability to recognize amino alcohols selectively on the basis of chirality and transform amino acids from an L-form into a D-form. Methods for the optical resolution of amino acid or amino alcohol and for the optical transformation of D- and L-forms of amino acids using the binaphthol derivative are also provided.

6 Claims, 2 Drawing Sheets

ALANINE RACEMASE CHIRAL BINAPHTHOL DERIVATIVE WITH POWERFUL HYDROGEN BOND DONOR, AND OPTICAL RESOLUTION AND OPTICAL TRANSFORMATION METHODS USING THE SAME

BACKGROUND OF THE INVENTION

1. Field of the Invention

The present invention relates to a binaphthol derivative useful for the optical resolution of amino acids or amino alcohols and for the optical transformation of amino acids from a D-form into an L-form, or vice versa.

The present invention also relates to a method of subjecting racemic amino acids or racemic amino alcohols to optical resolution using the above derivative, thus obtaining optically pure amino acids or optically pure amino alcohols.

The present invention also relates to a method of subjecting amino acids to optical transformation from a D-form into an L-form, or vice versa, using the above derivative.

2. Description of the Related Art

Optically pure amino acids and amino alcohols are widely used as ligands of asymmetric catalysts or as starting materials or intermediates necessary for synthesizing various pharmacerutical supplies and physiologically active substances, and are thus regarded as very important in industrial fields ((a) Coppola, G. M.; Schuster, H. F. Asymmetric Synthesis. Construction of Chiral Molecules Using Amino Acids; Wiley: N.Y., 1987; (b) Bergmeier, S. C. Tetrahedron 2000, 56, 2561-2576; (c) Noyori, R. Asymmetric Catalysis in Organic Synthesis; John Wiley & Sons: New York, 1994; (d) Helmchen, G.; Pfaltz, A. Acc. Chem. Res. 2000, 33, 336-345. (e) Ager, D. J.; Prakash, I.; Schaad, D. R. Chem. Rev. 1996, 96, 835-876).

With regard to the preparation of such optically pure amino alcohols, DE Unexamined Patent Publication No. 4341605 discloses a method of synthesizing optically pure amino alcohols from optically pure amino acids.

Unlike L-amino acids, D-amino acids do not naturally occur, but must be industrially synthesized using an enzymatic biocatalyst. In this case, attributable to the instability of the enzymatic biocatalyst and the high selectivity thereof to a substrate, the preparation costs are increased, and it is very difficult to produce various D-amino acids. Accordingly, various amino alcohols corresponding thereto are also difficult to produce, the preparation costs are very high, and the supply thereof is insufficient to meet the demand therefore.

Therefore, thorough research into methods of easily and inexpensively producing pure D-amino acids is continuously conducted ((a) Williams, R. M. In Synthesis of Optically Active a-Amino Acids; Baldwin, J. E., Ed.; Organic Chemistry Series; Pergamon Press: Oxford, 1989. (b) Williams, R. M.; Hendrix, J. A. Chem. Rev. 1992, 92, 889. (c) Duthaler, R. O. Tetrahedron 1994, 50, 1539. (d) Seebach, D.; Sting, A. R.; Hoffman, M. Angew. Chem., Int. Ed. Engl. 1996, 35, 2708. (e) Maruoka, K.; Ooi, T. Chem. Rev. 2003, 103, 3013.).

Favretto et. al. (Tetrahedron Lett. 2002, 43, 2581) proposed a method of synthesizing optically pure amino alcohol from chiral epoxide. However, this method is disadvantageous because of the use of expensive chiral epoxide and the poor yield, regioselectivity, and stereospecificity, thus making it difficult to realize industrial applications.

Recently, the optical resolution of amino alcohols by reactive extraction is regarded as an industrially attractive choice because it currently appears to be the most cost-effective process (Steensma, M.; Kuipers, N. J. M.; Haan, A. B.; Kwant, G. Chirality 2006, 18, 314.). Versatile chiral receptors were tested by N. Kuipers and Prelogs for chiral separation of a number of chemically related amino alcohols and amines by reactive extraction. However, the selectivities of most of the tested receptors were too low for commercial application, except azophenolic crown ether of Hirose whose selectivity approached to 5.0 (Naemura, K.; Nishioka, K.; Ogasahara K.; Nishikawa, Y.; Hirose, K.; To be, Y. Tetrahedron: Asymmetry 1998, 9, 563.).

Therefore, the present inventors have developed a method of forming an imine bond using a binaphthol derivative (Compound 1) having an aldehyde group to thereby recognize the chirality of a chiral amino alcohol or amino acid and transform L-amino acids into D-amino acids ((a) Park, H.; Kim, K. M.; Lee, A.; Ham, S.; Nam, W.; Chin, J. J. Am. Chem. Soc. 2007, 129, 1518-1519; (b) Kim, K. M.; Park, H.; Kim, H.; Chin, J.; Nam, W. Org. Lett., 2005, 7, 3525-3527).

Compound 1

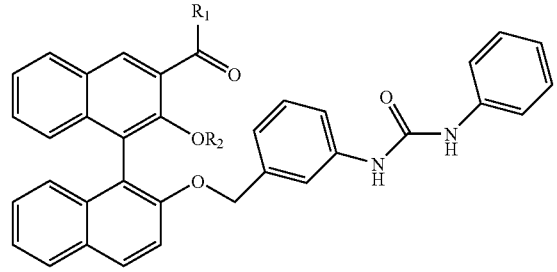

The binaphthol derivative (Compound 1) has been invented based on the reaction mechanism of a PLP compound ((a) Shaw, J. P.; Petsko, G. A. Ringe, D. Biochemistry, 1997, 36, 1329-1342; (b) Walsh, C. T. J. Biol. Chem. 1989, 264, 2393-2396) acting as a cofactor in an enzyme called amino acid racemase.

The binaphthol derivative (Compound 1) is useful for stereoselectively recognizing chiral amine through the formation of an imine bond and separating amino alcohol into respective optical isomers, are surprisingly able to convert DL-amino acids into D-amino acids, which is very useful to produce D-amino acids or optically pure non-natural amino acids by a novel way.

The binaphthol derivative (Compound 1) reacts also stereoselectively with amino alcohol, forming an imine compound, the selectivity thereof ranging from 1:3 to 1:5. However, in the case where the selectivity is high, amino alcohol may be more easily separated into respective optical isomers. Hence, the development of novel binaphthol derivatives having higher stereoselectivity is required for a more efficient industrialization process for the resolution of amino alcohols. Furthermore, Chiral binaphthol derivative having chemical properties such as high stereoselectivity and favorable solubility in chloroform or ethyl acetate are especially required to be applied to the reactive extraction process which is regarded as economically cost effective process.

SUMMARY OF THE INVENTION

Leading to the present invention, extensive and intensive research, conducted by the present inventors, led to the development of binaphthol derivatives (Formulas I~VI), having a guanidinium group or an imidazolium group able to form a powerful hydrogen bond with —OH or —$CO_2^-$ as well as an electrical bond through positive charges thereof.

Accordingly, the present invention provides a novel compound, which enables the more effective optical resolution of amino acids or amino alcohols having the D-form or the L-form.

In addition, the present invention provides a method of synthesizing a binaphthol derivative at high yield while solving problems with a conventional binaphthol derivative related to the production of many unnecessary by-products during the synthesis process.

DESCRIPTION OF THE PREFERRED EMBODIMENTS

Figure 1:
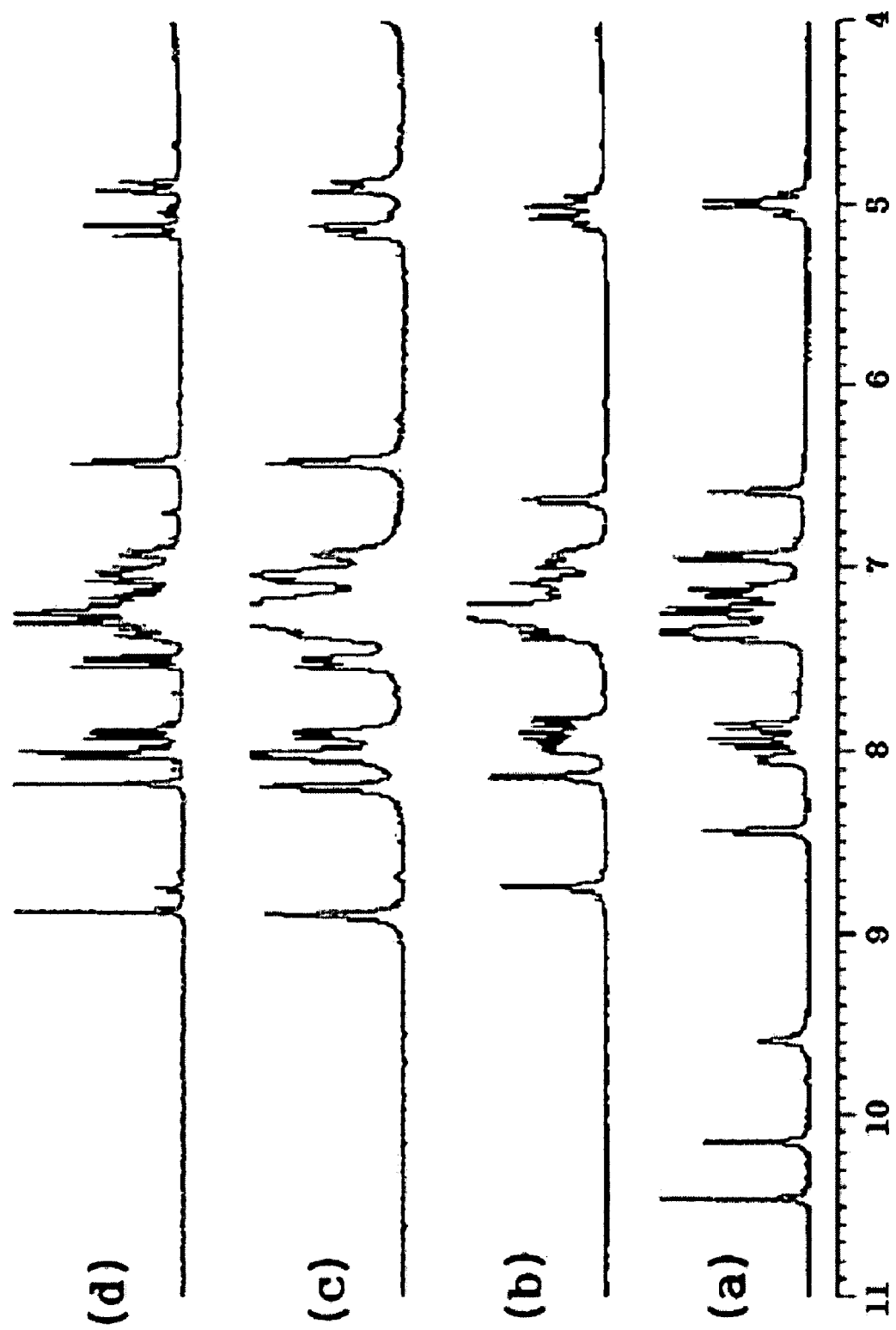
FIG. 1 is $^1$H NMR spectra in a $CDCl_3$ solvent, in which (a) is a spectrum of Compound 8, (b) is a spectrum of an imine compound formed through the reaction of Compound 8 and (S)-2-aminopropanol, (c) is a spectrum of an imine compound obtained through the reaction of Compound 8 and (R)-2-aminopropanol, and (d) is a spectrum of an imine compound obtained through the reaction of Compound 8 and 2 equivalents of (R,S)-2-aminopropanol.

The chiral selective recognition of amino alcohol or amino acid by Compound 1 is based on a difference in steric hindrance. That is, as seen in the following formulas, steric hindrance varies depending on the chirality of an imine compound which has a rigid structure by a hydrogen bond between the nitrogen of imine and —OH of phenol and a hydrogen bond between —OH or —$CO_2^-$ and a uryl group.

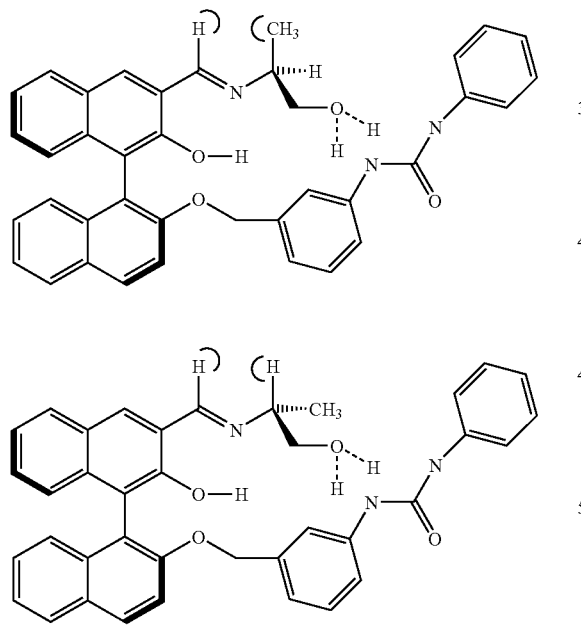

In order to increase chiral selectivity, the imine compound should be highly rigid. To this end, the bonding force between the —OH of amino alcohol and the uryl group of the binaphthol derivative should be larger. Thus, a hydrogen bond donor stronger than the uryl group is required.

Guanidinium or imidazolium cations behave as a hydrogen bond donor, and more powerfully form a hydrogen bond with —OH or —$CO_2^-$ than does the uryl group, leading to increased chiral selectivity.

Based on the above fact, the present inventors have designed novel binaphthol derivatives (Formulas I~VI) having a guanidinium group or an imidazolium group, and have succeeded in the synthesis thereof at high yield. Further, these novel derivatives have been confirmed to exhibit chiral selectivity superior to that of Compound 1, as a conventional binaphthol derivative.

The present invention is directed to compounds represented by Formulas I to VI below and derivatives thereof:

Formula I
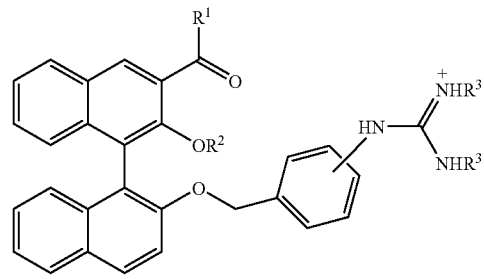

Formula II
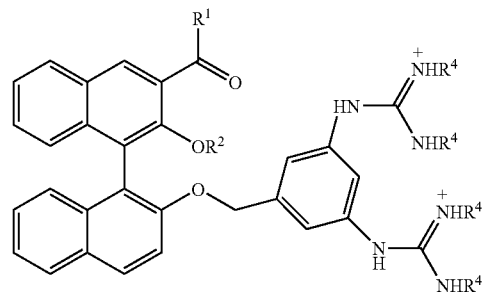

Formula III
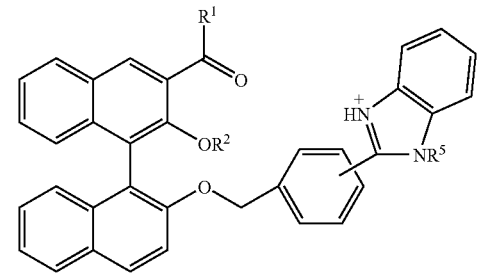

Formula IV
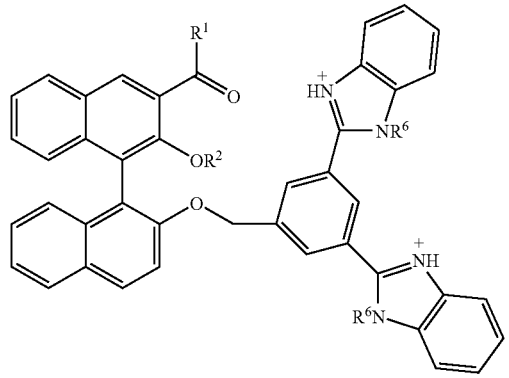

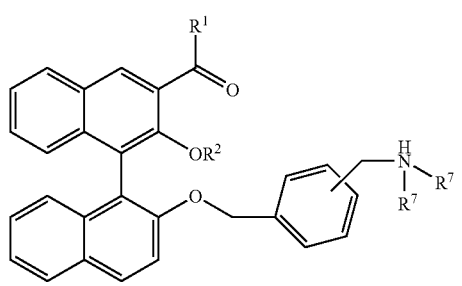

Formula V

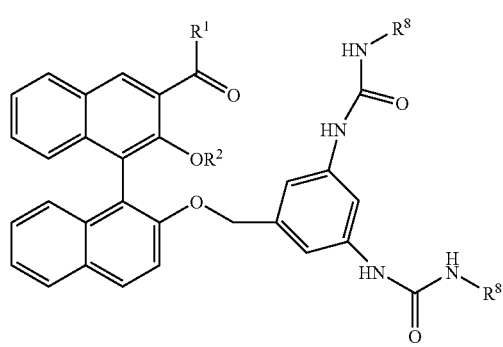

Formula VI in Formulas I to VI, R1 to R8 are each i) linear or branched alkyl substitutable with —OH, hydrogen, or halogen, ii) cyclic alkyl, alkenyl or alkynyl substitutable with —OH or halogen, or iii) aryl substitutable with —OH or halogen.

The above compounds have the following isomers.

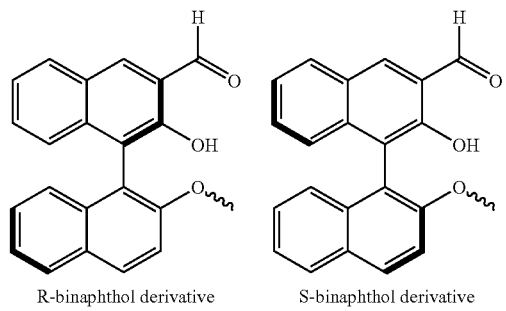

R-binaphthol derivative     S-binaphthol derivative

In addition, the present invention is directed to a method for the optical resolution of racemic amino alcohols or racemic amino acids using the compounds of Formulas I to VI.

In addition, the present invention is directed to a method for the optical transformation of amino acids from the D-form into the L-form or from the L-form into the D-form using the compounds of Formulas I to VI.

1. Synthesis of Compounds of Formulas I to VI

Below, the method of synthesizing the above compounds is described.

The method of synthesizing the compounds of Formulas I to VI is not particularly limited, but typically accords to the following reaction schemes.

(1) Preparation of Compound of Formula 1

The compound of Formula 1 may be synthesized according to Scheme 1 below:

Scheme 1

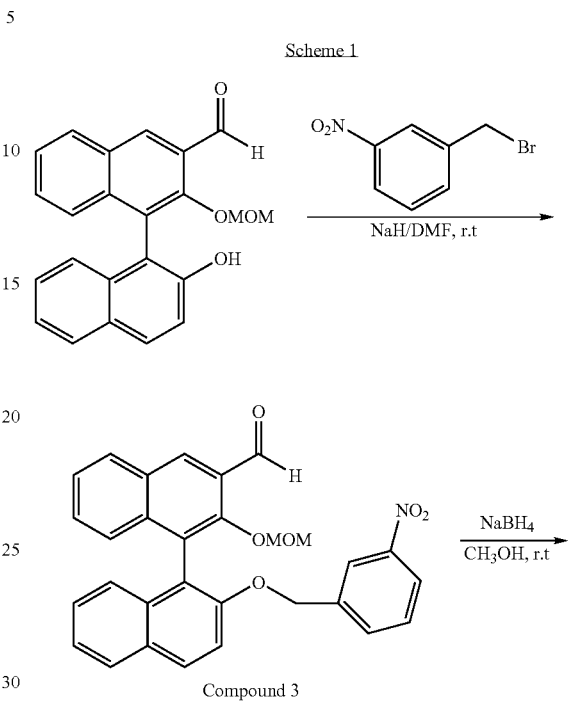

Compound 3

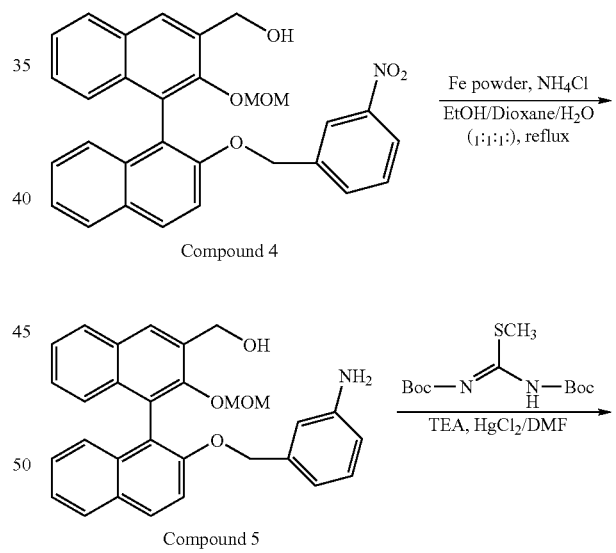

Compound 4

Compound 5

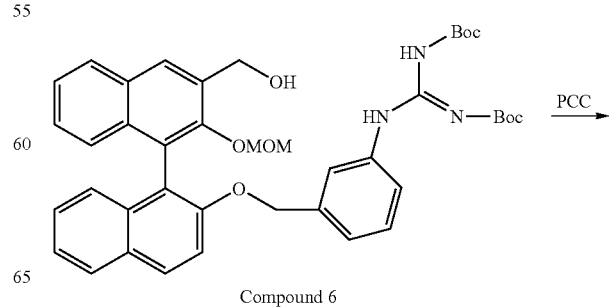

Compound 6

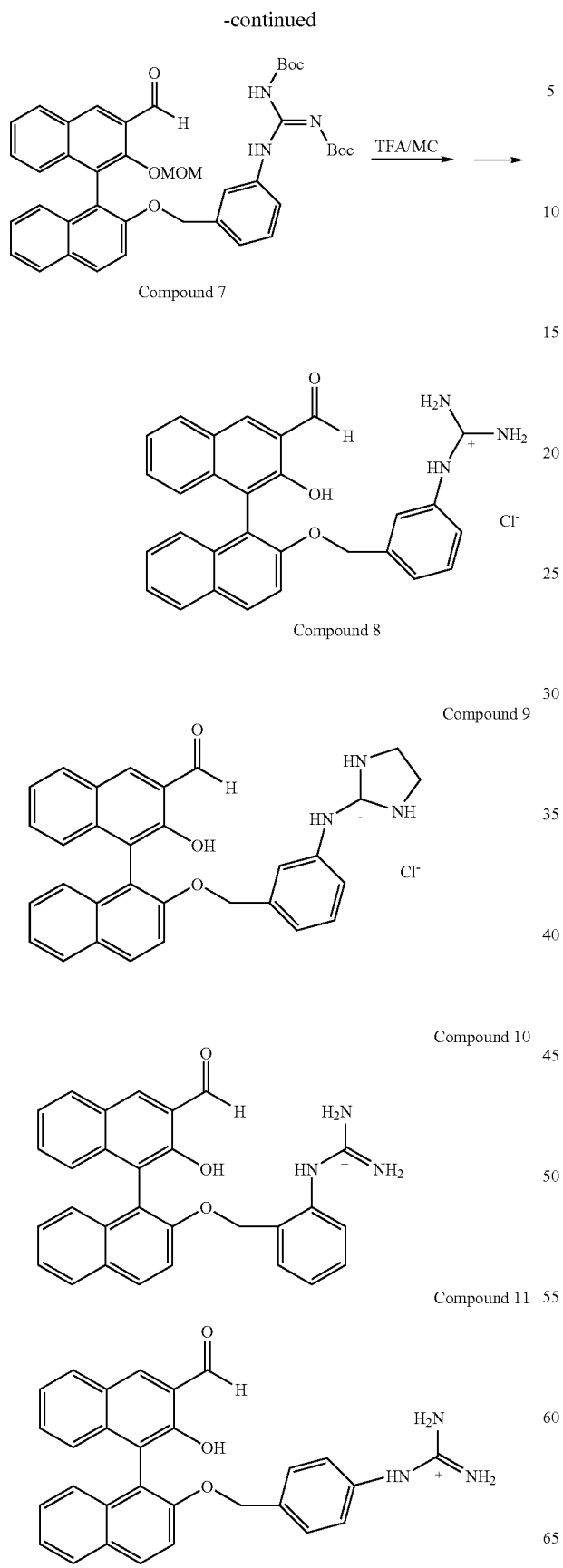
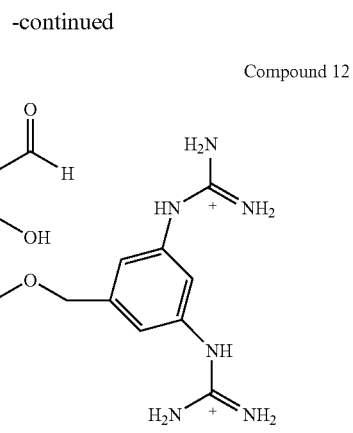

(in Scheme 1, MOM indicates methoxymethyl, Boc indicates t-butoxy carbonyl, PCC indicates pyridinium chlorochromate, and PPA indicates polyphosphoric acid).

Further, Compound 9 may be obtained according to Scheme 1 using N-Boc-2-methylthio-2-imidazoline, instead of 1,3-bis-BOC-2-methyl-2-thiopseudourea.

Further, Compound 10 and Compound 11 may be obtained according to Scheme 1 using 2-nitrobenzyl bromide and 4-nitrobenzylbromide, respectively, instead of 3-nitrobenzyl bromide.

All of the compounds thus obtained may be used for the optical isomer resolution of amino alcohols or amino acids and the chiral transformation of amino acids.

(2) Synthesis of Compound of Formula II

The compound of Formula II (Compound 12) may be obtained according to Scheme 1 using 2,4-dinitrobenzyl bromide instead of 3-nitrobenzyl bromide. This compound may also be used for the optical isomer resolution of amino alcohols or amino acids and the chiral transformation of amino acids.

In the prior patent (Korean Unexamined Patent Publication No. 2006-0088489), a binaphthol derivative having a uryl group is synthesized using 2,2'-binaphthol-3-aldehyde, instead of Compound 2, in which MOM is substituted at the 2-O position in Scheme 1. In this case, however, many by-products occur, and thus the yield of a final compound is remarkably decreased and the purity thereof is difficult to increase. Thus, in the present invention, the novel process of Scheme 1 has been developed.

Even in Schemes 2 to 5, the same principle is applied. That is, when a compound, in which MOM is substituted at the 2-O position of 2,2'-binaphthol or a derivative thereof, is used as a starting material, the yield and purity are preferably increased.

(3) Synthesis of Compounds of Formulas III and IV

The compounds of Formulas III and IV may be synthesized according to Schemes 2 and 3 below.

Scheme 2
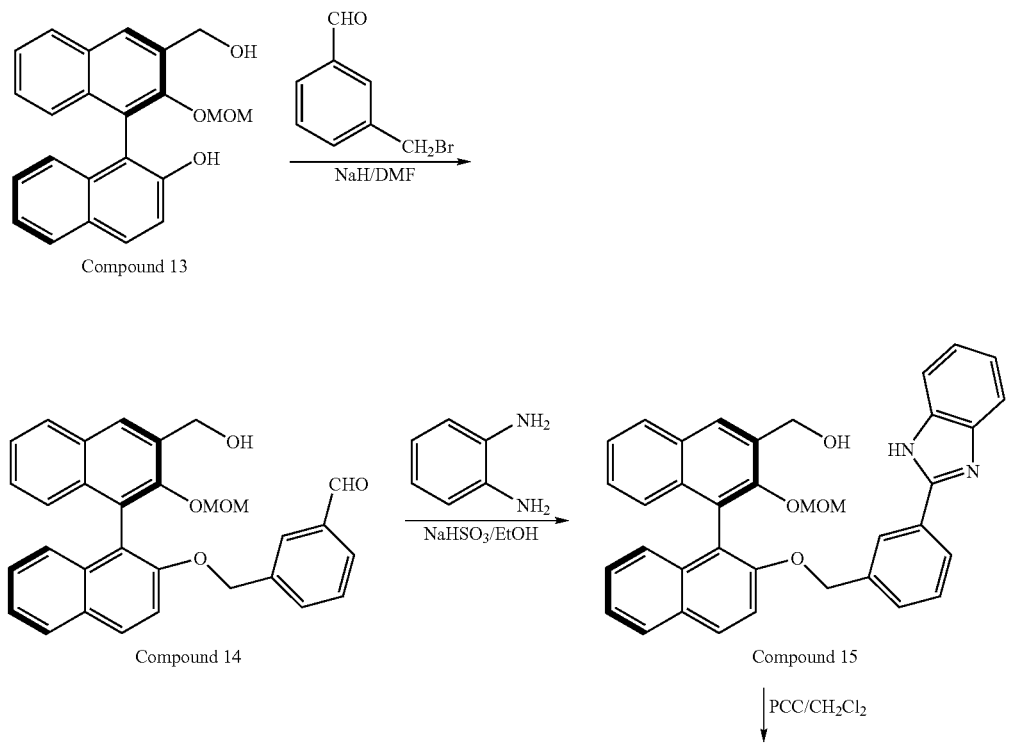
Scheme 3
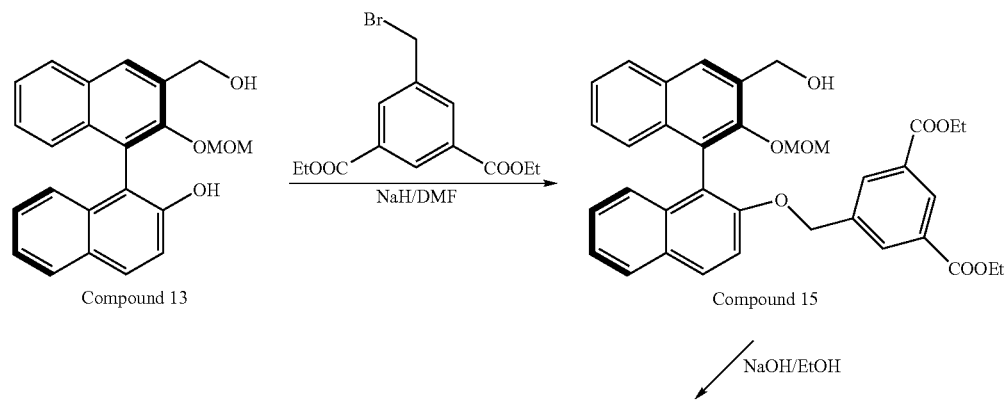

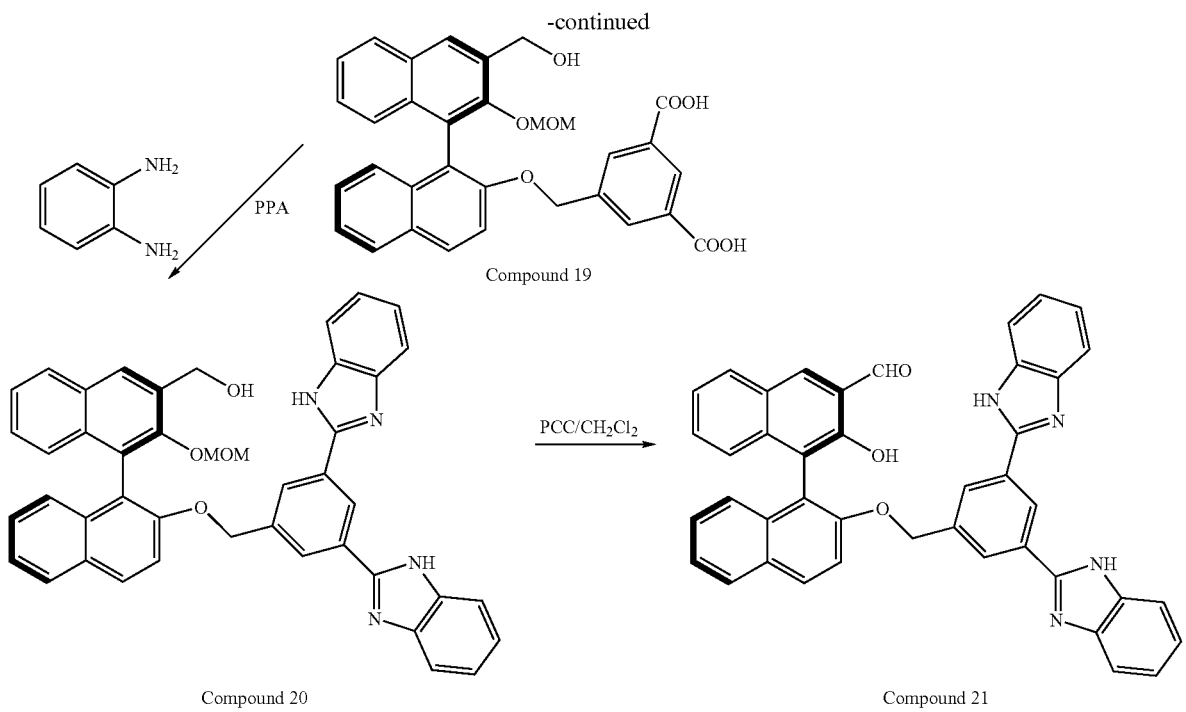

In the above process, when dialkylethylenediamine ((NH$_2$)RC=CR(NH$_2$)) is used instead of 1,2-diaminobenzene, various dialkylimidazolium derivatives corresponding thereto may be obtained.

(4) Synthesis of Compound of Formula V

The compound of Formula V may be synthesized according to Scheme 4 below:

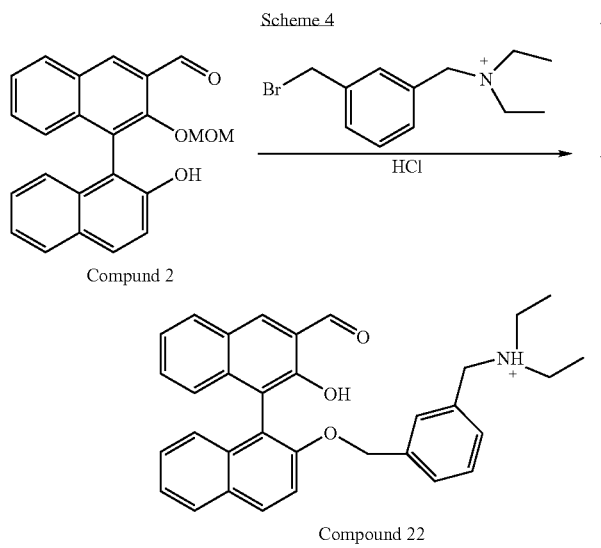

(5) Synthesis of Compound of Formula VI

The compound of Formula VI may be synthesized by subjecting a compound, obtained using dinitrobenzyl bromide instead of nitrobenzyl bromide in Scheme 1, to reduction from a nitro group into an —NH$_2$ group, and then to Scheme 5 below:

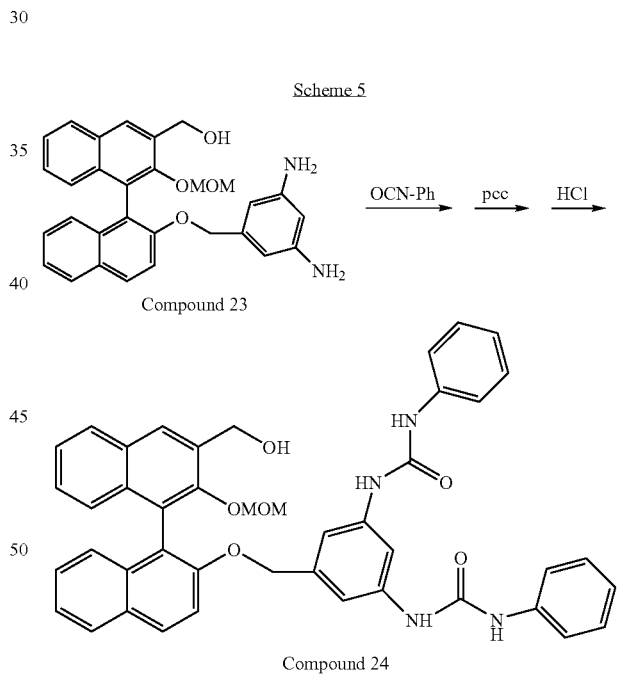

Although all the above reaction schemes are illustrated with S-binaphthol, they may also be applied to R-binaphthol.

2. Optical Resolution and Optical Transformation

The compounds of the present invention are useful for the optical resolution of racemic amino alcohols or racemic amino acids and the optical transformation of racemic amino acids.

(1) Optical Resolution of Racemic Amino Alcohol or Racemic Amino Acid

Amino alcohols that may be subjected to optical resolution using the compound of the present invention are represented by Formula VII below, in which an asymmetric carbon atom is present to thus form an optical isomer having an R-form or an S-form:

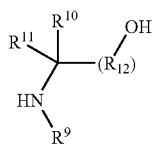

Formula VII wherein R9 to R12 are each independently a hydrogen-containing monovalent organic group or halogen, and preferably substituted or unsubstituted alkyl, substituted or unsubstituted alkenyl, substituted or unsubstituted cyclic alkyl, or substituted or unsubstituted aryl.

The compound of the present invention may be used for the optical resolution of amino acids represented by Formula VIII below:

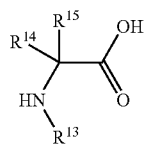

Formula VIII wherein R13 to R15 are each independently a hydrogen-containing monovalent organic group, and preferably substituted or unsubstituted alkyl, substituted or unsubstituted alkenyl, substituted or unsubstituted cyclic alkyl, or substituted or unsubstituted aryl.

As the method for optical resolution of racemic amino alcohols or racemic amino acids using the compounds of Formulas I to VI, any method may be used as long as it is known in the art. That is, a batch process using a solvent, or a column process, in which a column is filled with the compound, may be applied. Also, the reactive extraction process which is regarded as economically cost effective process may be applied. Further, amino alcohol or amino acid, which is subjected to primary optical resolution, may be repeatedly subjected to optical resolution, if required, thereby obtaining amino alcohol or amino acid having higher optical purity.

3. Optical Transformation of Racemic Amino Acid

Using the compound of the present invention, amino acid of Formula VIII may be transformed from a D-form into an L-form, or vice versa. In the case of the S-binaphthol derivative of the present invention, an L-amino acid may be transformed into a D-amino acid. In the case of the R-binaphthol derivative, a D-amino acid may be transformed into an L-amino acid. This phenomenon is considered to be due to the recognition of chirality of the chiral compound.

A better understanding of the present invention may be obtained through the following examples, which are set forth to illustrate, but are not to be construed as the limit of the present invention.

EXAMPLE 1

Synthesis of S-Binaphthol Derivative of Compound 8

(1) Preparation of Compound 3 ((S)-1-methoxymethyl-1'-(3-nitrobenzyl)-bi-2-naphtholaldehyde)

(S)-1-methoxymethyl-bi-2-naphtholaldehyde (Compound 2) (0.6 g, 1.67 mmol) was dissolved in 5 ml of DMF, after which the solution was added with NaH (0.081 g, 2.0 mmol) and was then stirred for 10 min. Further, the stirred solution was added with 3-nitrobenzyl bromide (0.434 g, 2.0 mmol) and was then stirred at room temperature for 4 hours, thus obtaining Compound 3.

Compound 3

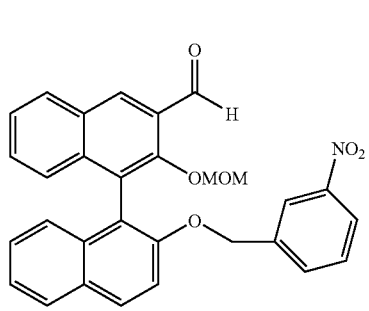

Yield: 95%. $^1$H NMR (CDCl$_3$, 250 MHz): 10.60 (s, 1H, CHO), 8.61 (s, 1H), 8.03-7.83 (m, 5H), 7.48-7.20 (m, 9H), 5.19 (dd, 2H, benzylic), 4.73 (dd, 2H, —OCH$_2$O—), 2.89 (s, 3H, —OCH$_3$).

(2) Preparation of Compound 4 ((S)-1-methoxymethyl-1'-(3-nitrobenzyl)-2-hydroxymethyl-binaphthol)

To Compound 3 (0.643 g, 1.3 mmol) in a methanol solution, NaBH$_4$ (60 mg, 1.56 mmol) was added, thus obtaining Compound 4.

Compound 4

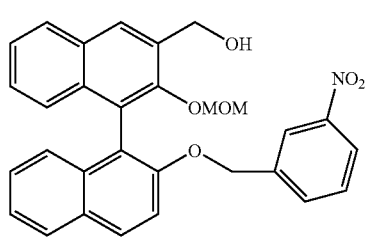

Yield: 98%. $^1$H NMR (CDCl$_3$, 250 MHz): 8.02-7.79 (m, 6H), 7.43-7.11 (m, 9H), 5.11 (dd, 2H, —OCH$_2$Ar), 4.95 (s, 2H, ArCH$_2$OH), 4.55 (dd, 2H, —OCH$_2$O—), 3.57 (s, br, 1H, OH), 3.12 (s, 3H, OCH$_3$).

(3) Preparation of Compound 5 ((S)-1-methoxymethyl-1'-(3-aminobenzyl)-2-hydroxymethyl-binaphthol)

A solution of ethanol/dioxane/water mixed at 1:1:1 was added with Compound 4 (0.646 g, 1.3 mmol), iron powder (0.504 g, 9.1 mmol), and ammonium chloride (0.126 g, 2.34 mmol), and was then allowed to react, thus obtaining Compound 5.

Compound 5

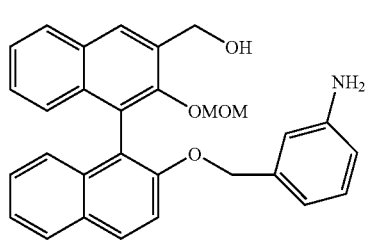

Yield: 95%. $^1$H NMR (CDCl$_3$, 250 MHz): 8.03-8.78 (m, 4H), 7.49-7.24 (m, 7H), 6.96 (m, 1H), 6.48 (m, 2H), 6.13 (s, 1H), 5.04-4.86 (m, 4H), 4.60 (dd, 2H, —OCH2O—), 3.51 (br, 3H, NH$_2$ and OH), 3.18 (s, 3H, —OCH$_3$).

(4) Preparation of Compound 6 ((S)-1-methoxymethyl-1'-(3-(4,5-dihydro-1H-imidazole-2-diaminobenzyl)-2-hydroxymethyl-binaphthol)

50 ml of an AcOH/EtOH (1:9 v/v) solution of Compound 5 (0.56 g, 1.2 mmol) and 1,3-bis-BOC-2-methyl-2-thiopseudourea (0.35 g, 1.4 mmol) was heated for 16 hours, thus obtaining Compound 6.

Compound 6

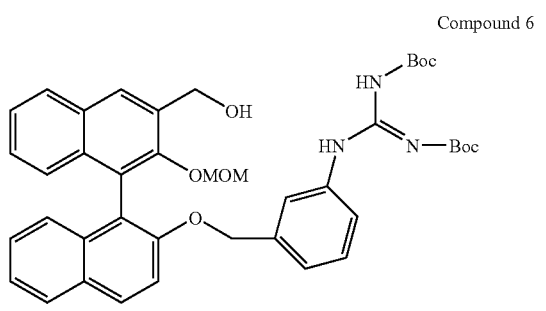

Yield: 85%. $^1$H NMR (CDCl$_3$, 250 MHz): 8.11 (s, 1H), 7.96 (d, 1H, J=9.0 Hz), 7.87 (s, 2H, J=9.0 Hz), 7.47 (d, 1H, J=9.0 Hz), 7.38-7.02 (m, 7H), 6.83 (d, 1H), 6.66 (d, 1H, J=7.5 Hz), 6.57 (s, 1H), 5.13-4.79 (m, 4H), 4.51 (s, 2H, —OCH$_2$O—), 4.16 (br, 3H), 3.43 (s, 4H, guanidine CH$_2$), 2.96 (s, 3H, —OCH$_3$).

(5) Preparation of Compound 8 ((S)-1-1'-(3-(4,5-dihydro-1H-imidazole-2-diamino)benzyl)-bi-2-naphtholaldehyde)

Compound 6 was treated with PCC, after which MOM was separated with an HCl solution, thus obtaining Compound 8.

Compound 8

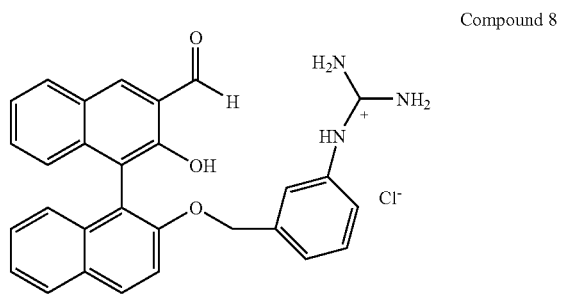

Yield: 95%. $^1$H NMR (DMSO-d$_6$, 250 MHz): 10.40 (s, br, 1H, NH), 10.36 (s, 1H, CHO), 10.15 (s, br, OH), 8.68 (s, 1H), 8.23-8.07 (m, 4H), 7.97 (d, 1H, J=8.0 Hz), 7.64 (d, 1H, J=9.0 Hz), 7.45-7.22 (m, 5H), 7.55-6.99 (m, 4H), 6.87 (s, 1H), 5.21 (s, 2H, benzylic CH$_2$), 3.63 (s, 4H, guanidine CH$_2$).

EXAMPLE 2

Synthesis of R-Binaphthol Derivative of Compound 8

The title compound was synthesized in the same manner as in Example 1, with the exception that (R)-1-methoxymethyl-bi-2-naphtholaldehyde was used instead of (S)-1-methoxymethyl-bi-2-naphtholaldehyde.

EXAMPLE 3

Synthesis of S-Binaphthol Derivative of Compound 9

The title compound was synthesized in the same manner as in Example 1, with the exception that N-Boc-2-methylthio-2-imidazoline was used instead of 1,3-bis-BOC-2-methyl-2-thiopseudourea.

Compound 9

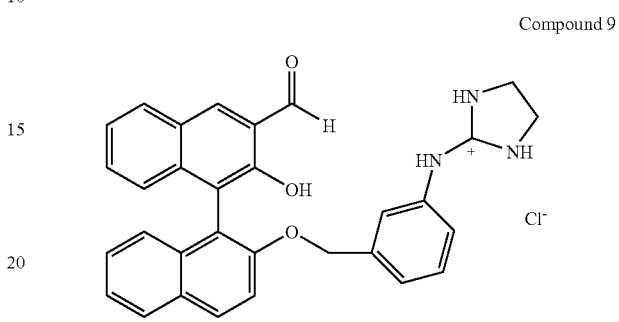

1H NMR (DMSO-d$_6$, 250 MHz): 10.34 (s, 1H, CHO), 10.26 (s, 1H, NH), 9.02 (s, 1H, NH), 8.67 (s, 1H), 8.17-8.07 (m, 2H), 7.97 (d, 1H, J=7.9 Hz), 7.63 (d, 1H, J=9.1 Hz), 7.45-7.20 (m, 9H), 7.07-6.96 (m, 4H), 6.81 (s, 1H), 5.19 (s, 2H, benzylic CH$_2$).

EXAMPLE 4

Synthesis of R-Binaphthol Derivative of Compound 9

The title compound was synthesized in the same manner as in Example 3, with the exception that (R)-1-methoxymethyl-bi-2-naphtholaldehyde was used instead of (S)-1-methoxymethyl-bi-2-naphtholaldehyde.

EXAMPLE 5

Synthesis of S-Binaphthol Derivative of Compound 17

(1) Preparation of Compound 14

(S)-1-methoxymethyl-2-hydroxymethyl-binaphthol (Compound 13, 0.41 mmol) was added with NaH (11 mg, 0.46 mmol) and 3-(bromomethyl)benzaldehyde (82 mg, 0.42 mmol), and was then stirred in DMF thus obtaining Compound 14.

Compound 14

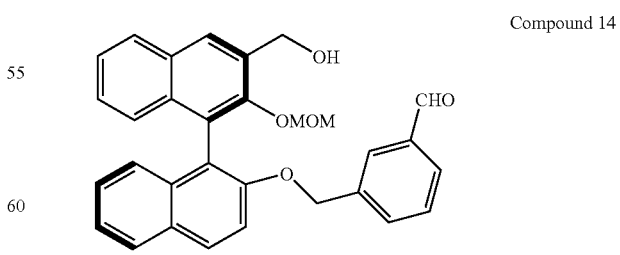

Yield: 80%. $^1$H NMR (CDCl$_3$, 250 MHz): 9.72 (s, 1H, —CHO), 7.88-8.02 (m, 4H), 7.13-7.64 (m, 1H), 5.06-5.20 (dd, 2H, MOM-CH$_2$), 4.93 (d, 2H, —CH$_2$OH), 4.48-4.61 (dd, 2H, 2-O-benzylic CH$_2$), 3.15 (s, 3H, —OCH$_3$).

(2) Preparation of Compound 15

Compound 14 (300 mg, 0.627 mmol), para-phenylene diamine (75 mg, 0.693 mmol), and NaHSO$_3$ (65 mg, 0.627 mmol) were boiled in an ethanol solution for 10 hours, thus obtaining Compound 15.

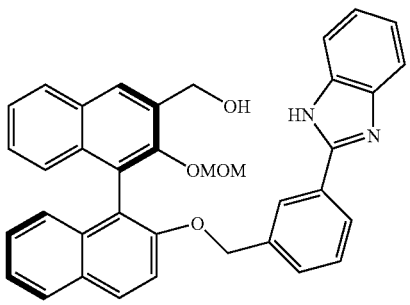

Compound 15

Yield: 76%. $^1$H NMR (CDCl$_3$, 250 MHz): 10.69 (s, 1H, —OH), 7.18-8.07 (m, 20H), 5.19-5.27 (dd, 2H, —CH$_2$), 4.99-5.04 (d, 2H, —O—CH$_2$), 4.60-4.70 (dd, 2H, —O—CH$_2$—OCH$_3$), 3.14 (s, 3H, —O—CH$_2$—OCH$_3$).

(3) Preparation of Compound 17

Compound 15 was treated with PCC, and was then added with HCl, thus obtaining Compound 1-7.

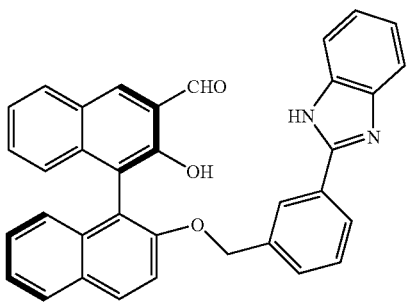

Compound 17

Yield: 84%. $^1$H NMR (DMSO-d$_6$, 250 MHz): 12.81 (br, 1H, —OH), 10.33 (s, 1H, —CHO), 8.62 (s, 1H), 6.96-8.09 (m, 20H), 5.29 (s, 2H, —OCH$_2$—).

EXAMPLE 6

Synthesis of S-Binaphthol Derivative of Compound 22 ((S)-1-Hydroxy-1'-(3-Diethylaminomethylbenzyl)-2-Aldehyde-Binaphthol)

To DMF of an ice bath, NaH (2.4 equiv. 0.12) and Compound 2 (0.43 g, 1.12 mmol) were sequentially added. After 1 hour, this solution was added with diethylaminomethyl benzylbromide (0.42 g, 1.23 mmol) and was then allowed to react, thus obtaining the following compound ((S)-1-methoxymethyl-1'-(3-diethylaminomethylbenzyl)-2-aldehyde-binaphthol).

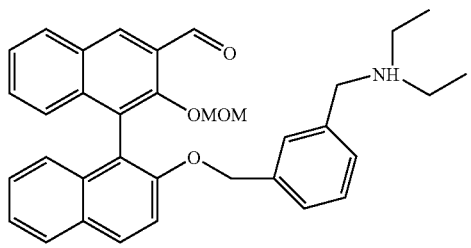

The above compound ((S)-1-methoxymethyl-1'-(3-diethylaminomethylbenzyl)-2-aldehyde-binaphthol) (0.2 g, 0.37 mmol) was added with hydrogen chloride in ethanol, and was then heated, thus obtaining Compound 22.

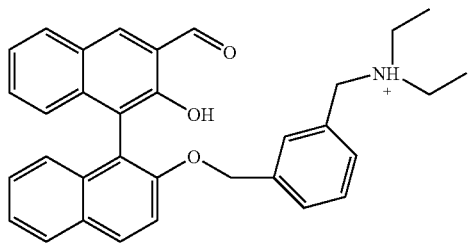

Compound 22

Yield: 90%. $^1$H NMR (DMSO-d$_6$, 250 MHz); δ0.48 (s, 1H, —CHO), 10.35 (s, 1H, —OH) 8.80 (s, 1H, —CH), 8.23~7.14 (m, 14H), 5.34 (s, 2H, —OCH$_2$—), 4.16 (s, 2H, —NCH$_2$—), 3.04 (q, 4H, —CH$_2$ of ethyl), 1.26 (t, 6H, —CH$_3$ of ethyl)

EXAMPLE 7

Optical Resolution of Amino Alcohol using Compound 8 and Compound 9

(1) Test

The optical resolution of amino alcohol using the binaphthol derivative of the present invention was tested as follows.

As the binaphthol derivative, Compound 8 (Examples 1 and 2) and Compound 9 (Examples 3 and 4) were used. The racemic amino alcohol was exemplified by four amino alcohols, including aminopropanol (Table 1 below).

Into an NMR tube, 0.7 ml of CDCl$_3$, 0.04 mmol (R,S)-2-aminopropanol, in which the R-form and the S-form were mixed at 1:1, and 0.02 mmol binaphthol derivative were added, after which $^1$H-NMR was measured. The results are shown in (d) of FIG. 1.

For comparison, the $^1$H-NMR spectrum of Compound 8 alone is shown in (a) of FIG. 1.

The imine compound was formed within 5 min, and thus reached equilibrium.

Further, the R-form and the S-form were each added in the same amount, after which $^1$H NMR was measured and the positions of the peaks of the racemic mixture were designated. The $^1$H NMR spectrum of the imine compound resulting from Compound 8 and (S)-2-aminopropanol is shown in (b) of FIG. 1, and the $^1$H NMR spectrum of the imine compound resulting from Compound 8 and (R)-2-aminopropanol is shown in (c) of FIG. 1.

The chiral selectivity was determined by integrating the peak corresponding to the R-form and the peak corresponding to the S-form.

(2) Results

As is apparent from the $^1$H NMR of (d) of FIG. 1 for the imine compound, resulting from Compound 8 and racemic aminopropanol, selectivity is found between the R-form and the S-form. When originating from R-amino alcohol and S-amino alcohol, the imine proton peaks appear at 8.95 ppm and 8.80 ppm, respectively, as seen in (b) and (c) of FIG. 1. Thus, in the spectrum of (d) of FIG. 1, the intensities of the peaks at 8.95 ppm and 8.80 ppm were measured, thereby quantitatively analyzing the R-form and the S-form, used for forming the imine bond with Compound 8.

The $^1$H NMR spectrum of (d) demonstrates that the peak corresponding to R-imine is 5.0 times higher than the peak corresponding to S-imine, indicating that R-amino alcohol can form an imine bond with Compound 8 5.0$^2$=25 times more than can S-amino alcohol.

In addition, when Compound 9 and other amino alcohols were tested in the same manner as above, good chiral selectivity was also realized. The results are summarized in Table 1 below.

COMPARATIVE EXAMPLE 1

Optical Resolution of Amino Alcohol Using Known Binaphthol Derivative

The optical resolution of amino alcohol was tested as in Example 8, with the exception that the following binaphthol derivative, known in the prior patent (Korean Unexamined Patent Publication No. 2006-0088489), was used. The results are also summarized in Table 1 below.

TABLE 1

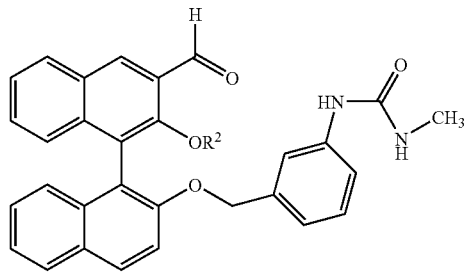

Chiral Selectivity for Amino Alcohol in Example 8 (Compound 8 and Compound 9) and Comparative Example 1 ($K_R$ = imine formation constant by R-amino alcohol; $K_S$ = imine formation constant by S-amino alcohol)

| | $K_R/K_S$ | | |
|---|---|---|---|
| | Ex. 8 | | |
| Amino Alcohol | Compound 8 | Compound 9 | C. Ex. |
| 2-Amino-1-Propanol | 13.7 | 13.7 | 3.8 |
| 2-Amino-1-Butanol | 17.6 | 17.6 | 3.1 |
| 2-Amino-2-Phenylethanol | 25.0 | 25.0 | 4.6 |
| 2-Amino-3-Phenyl-1-Propanol | 16.8 | 16.8 | 4.9 |

EXAMPLE 8

Optical Transformation of L-Amino Acid into D-Amino

Acid using Compound 8 and Compound 9

(1) Test

The optical transformation of amino acid using the binaphthol derivative of the present invention was tested as follows.

As the binaphthol derivative, Compound 8 (Examples 1 and 2) and Compound 9 (Examples 3 and 4) were used, and the racemic amino acid was exemplified by six amino acids, including triethylamine (Table 2 below).

Into an NMR tube, 0.7 ml of DMSO-$d_6$, 0.022 mmol L-amino acid, 0.08 mmol triethylamine, and 0.02 mmol binaphthol derivative were added, and $^1$H-NMR was measured.

Immediately after the L-amino acid completely reacted with the binaphthol derivative, an imine was formed.

Then, $^1$H-NMR was measured over time, from which the L-amino acid was confirmed to have been transformed into a D-amino acid.

Figure 2:
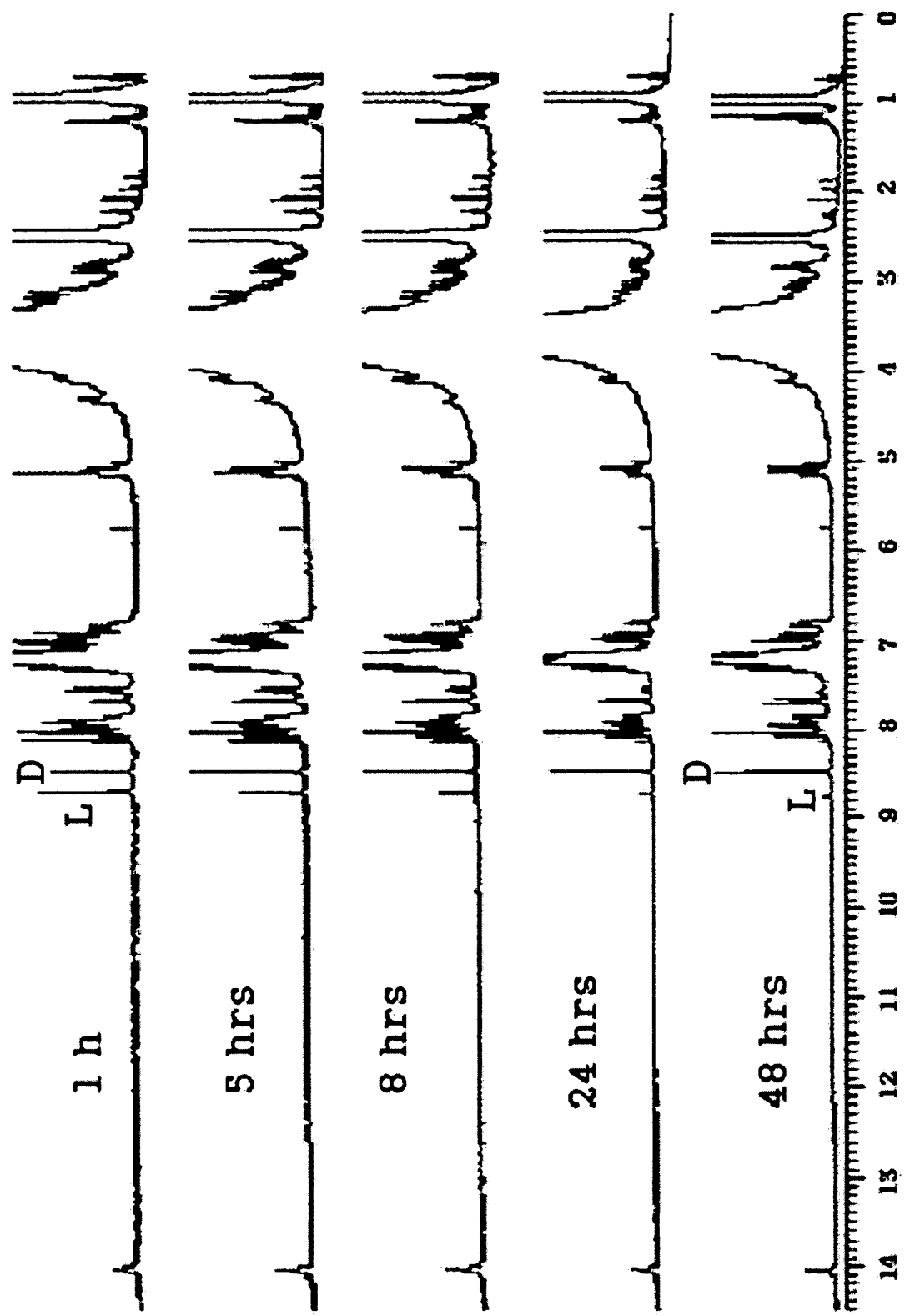
FIG. 2 is $^1$H NMR spectra of an imine compound formed through the reaction of Compound 8 and L-phenylalanine in the presence of 4 equivalents of $Et_3N$, sequentially showing states after reaction times of 1 hour, 5 hours, 8 hours, 24 hours, and 48 hours, in a downward direction.

FIG. 2 illustrates the $^1$H NMR showing the transformation of L-phenylalanine into D-phenylalanine using Compound 8.

The upper first spectrum of FIG. 2 shows $^1$H NMR of the imine compound, formed 1 hour after the reaction of the S-binaphthol derivative of Compound 8 and the L-phenylalanine in the presence of 4 equivalents of Et$_3$N, the $^1$H NMR spectra thereunder sequentially showing states after reaction times of 5 hours, 8 hours, 24 hours, and 48 hours.

As shown in these spectra, new peaks appear just after the reaction. These peaks coincide with the peaks of imine formed through the reaction of Compound 8 and D-phenylalanine. After 48 hours, the peaks detected in L-phenylalanine almost disappear, whereas the peaks detected in D-phenylalanine predominate. This means that L-phenylalanine was transformed into D-phenylalanine.

In FIG. 2, in the compound formed through the reaction of Compound 8 and L-alanine, about 97.7% of L-phenylalanine can be seen to have been transformed into D-phenylalanine (L:D=1:42, according to the calculation of the area of the peaks) after about 48 hours. However, almost no D-phenylalanine was transformed into L-phenylalanine. This is because Compound 8 is the S-binaphthol derivative. Thus, if the R-binaphthol derivative is used, D-amino acid can be transformed into L-amino acid.

Consequently, using the compound of the present invention, only one isomer of optically pure D-amino acid or L-amino acid from racemic amino acid can be effectively obtained.

Other amino acids were tested in the same manner as above, using Compound 8 and Compound 9. As the results, the final ratio of L-amino acid and D-amino acid is summarized in Table 2 below.

COMPARATIVE EXAMPLE 2

Optical Transformation of L-Amino Acid into D-Amino Acid using Known Binaphthol Derivative The optical transformation of amino acid was tested in the same manner as in Example 9, with the exception that the binaphthol derivative of Comparative Example 1 was used. The results are also summarized in Table 2 below.

TABLE 2

Ratio of D-Amino Acid/L-Amino Acid in Equilibrium (measured by $^1$H NMR Integration ratio)

| Amino Alcohol | $K_R/K_S$ | | |
|---|---|---|---|
| | Ex. 8 | | |
| | Compound 8 | Compound 9 | C.Ex. |
| histidine | 50/1 | — | 13.9/1 |
| tyrosine | 20/1 | 25/1 | 12.3/1 |
| phenylalanine | 42/1 | 11/1 | 11.1/1 |
| serine | 27/1 | — | 10.6/1 |
| glutamine | 18/1 | — | 14.8/1 |
| asparagines | 17/1 | — | 13.0/1 |

The reason why the compounds of the present invention are bonded with amino alcohol with high chiral selectivity and cause L-amino acid to be transformed into D-amino acid is considered to be the same as in the case of the prior patent (Korean Unexamined Patent Publication No. 2006-0088489).

However, Compound 8 and Compound 9 of the present invention have much higher selectivity than the compound of the prior patent. This is because the guanidinium group of Compound 8 and Compound 9 is cationic, such that a more powerful hydrogen bond can result.

It is deemed that the powerful hydrogen bond between the carboxylate group ($-CO_2^-$) of amino acid and the guanidinium makes the entire imine structure rigid, to thus increase chiral selectivity. For instance, the compound of Formula VI has two uryl groups, and thus can be more powerfully bonded with $-OH$ or $-CO_2^-$ than a compound having one uryl group.

According to the present invention, the binaphthol derivative can be strongly bonded with a hydroxyl group ($-OH$) and a carboxylate group ($-CO_2^-$) of amino alcohol, thus greatly increasing the ability to recognize the chirality of chiral amino alcohols or amino acids compared to conventional techniques, thereby advantageously facilitating the industrial application thereof.

Whereas a conventional binaphthol derivative (Compound 1) having a uryl group forms about 4~5 times more imine with R-amino alcohol than with S-amino alcohol, Compound 8, having a cationic guanidinium group according to the present invention, can form about 20~30 times more imine with the R-form than with the S-form.

In the present invention, the synthesis efficiency of binaphthol derivatives able to recognize the chirality of amino alcohols or amino acids and realize the mutual transformation of L-amino acid and D-amino acid can be drastically increased, thereby economically synthesizing binaphthol derivatives.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A binaphthol derivative selected from the group consisting of compounds represented by Formulas I, II, V, and VI below:

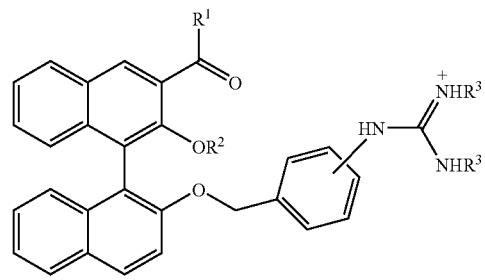

Formula I

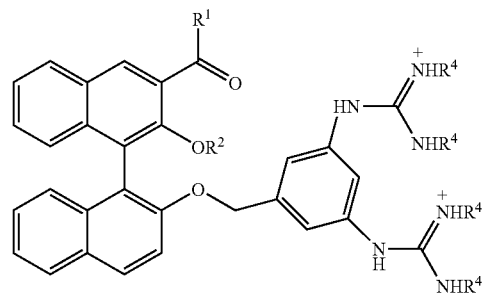

Formula II

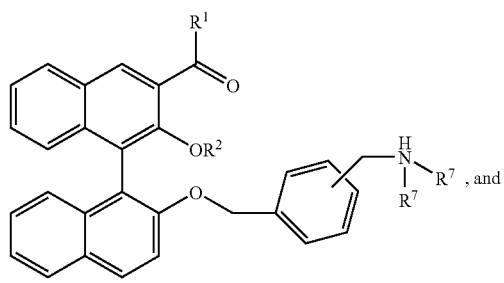

Formula V

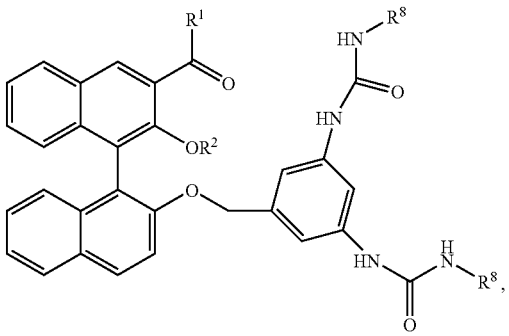

Formula VI wherein R1 to R4, R7, and R8 are each:
(i) linear or branched alkyl groups substitutable with $-OH$, hydrogen or halogen,
(ii) cyclic alkyl, alkenyl or alkynyl groups substitutable with $-OH$ or halogen, or
(iii) aryl groups substitutable with $-OH$ or halogen.

2. A method for optical resolution of a racemic amino alcohol represented by Formula VII below or a racemic amino acid represented by Formula VIII below:

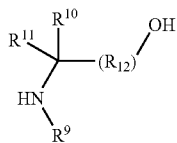

Formula VII wherein R9 to R12 are each independently a hydrogen-containing monovalent organic group or halogen; and

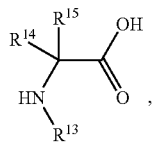

Formula VIII wherein R13 to R15 are each independently a hydrogen-containing monovalent organic group, the method comprising:

providing the compound of claim 1; and optically resolving the racemic amino alcohol represented by Formula VII or the racemic amino acid represented by Formula VIII using the compound of claim 1.

3. The method as set forth in claim 2, wherein the R9 to R12 are each independently, as the hydrogen-containing monovalent organic group, substituted or unsubstituted alkyl, substituted or unsubstituted alkenyl, substituted or unsubstituted cyclic alkyl, or substituted or unsubstituted aryl.

4. The method as set forth in claim 2, wherein the R13 to R15 are each independently, as the hydrogen-containing monovalent organic group, substituted or unsubstituted alkyl, substituted or unsubstituted alkenyl, substituted or unsubstituted cyclic alkyl, or substituted or unsubstituted aryl.

5. A method for optical transformation of an amino acid represented by Formula VIII below from a D-form into an L-form or from the L-form into the D-form:

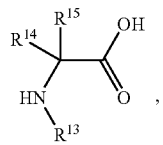

Formula VIII wherein R13 to R15 are each independently a hydrogen-containing monovalent organic group, the method comprising:

providing the compound of claim 1; and optically transforming the amino acid represented by Formula VIII from a D-form into an L-form or from the L-form into the D-form using the compound of claim 1.

6. The method as set forth in claim 5, wherein the R13 to R15 are each independently, as the hydrogen-containing monovalent organic group, substituted or unsubstituted alkyl, substituted or unsubstituted alkenyl, substituted or unsubstituted cyclic alkyl, or substituted or unsubstituted aryl.

* * * * *